(12) United States Patent
Fedele et al.

(10) Patent No.: US 8,940,775 B2
(45) Date of Patent: Jan. 27, 2015

(54) USE OF DERIVATIVES OF PENTAPHYRINE AS ANTIMICROBIAL AND DISINFECTANT AGENTS

(75) Inventors: Rosalisa Fedele, Pradamano (IT); Clara Comuzzi, Tricesimo (IT); Giada Rossi, Pasian di Prato (IT); Daniele Goi, Udine (IT)

(73) Assignee: Universita' Degli Studi di Udine, Udine (IT)

( * ) Notice: Subject to any disclaimer, the term of this patent is extended or adjusted under 35 U.S.C. 154(b) by 2 days.

(21) Appl. No.: 13/822,149

(22) PCT Filed: Sep. 13, 2011

(86) PCT No.: PCT/IB2011/053992
§ 371 (c)(1),
(2), (4) Date: Mar. 11, 2013

(87) PCT Pub. No.: WO2012/035489
PCT Pub. Date: Mar. 22, 2012

(65) Prior Publication Data
US 2013/0172396 A1 Jul. 4, 2013

(30) Foreign Application Priority Data
Sep. 13, 2010 (IT) .............................. PD2010A0271

(51) Int. Cl.
| | | |
|---|---|---|
| A01N 43/64 | (2006.01) | |
| A61K 31/41 | (2006.01) | |
| A01N 43/36 | (2006.01) | |
| A61K 31/40 | (2006.01) | |
| A01N 43/38 | (2006.01) | |
| C07D 487/22 | (2006.01) | |
| A61K 31/397 | (2006.01) | |

(52) U.S. Cl.
CPC ............ *C07D 487/22* (2013.01); *A61K 31/397* (2013.01)
USPC ............................ 514/359; 514/408; 514/410

(58) Field of Classification Search
USPC ......................................... 514/359, 408, 410
See application file for complete search history.

(56) References Cited

PUBLICATIONS

Stefano Banfi, et al., "Antibacterial activity of tetraaryl-porphyrin photosensitizers: An in vitro study on Gram negative and Gram positive bacteria," Journal of Photochemistry and Photobiology B: Biology, vol. 85, pp. 28-38 (2006).
Clara Colmuzzi, et al., "Spectroscopic characterization of the oxidation control of the iso-pentaphyrin/pentaphyrin system," Tetrahedron, vol. 62, pp. 8147-8151 (2006).
A. Oliveira, et al., "Porphyrin derivatives as photosensitizers for the inactivation of *Bacillus cereus* endospores," Journal of Applied Microbiology, vol. 106, pp. 1986-1995 (2009).
Michela Magaraggia, et al., "Treatment of microbiologically polluted aquaculture waters by a novel photochemical technique of potentially low environmental impact," Journal of Environmental Monitoring, vol. 8, pp. 923-931(2006).
Clara Comuzzi, et al., "Synthesis and Biological Evaluation of New Pentaphyrin Macrocycles for Photodynamic Therapy," J. Med. Chem., vol. 49, pp. 196-204 (2006).
Valentina Rapozzi, et al., "Small Interfering RNA-Mediated Silencing of Glutathione-S-Transferase A1 Sensitizes Hepatic Carcinoma Cells to Photogynamic Therapy with Pentaphyrins," ChemMedChem, vol. 3, pp. 565-568 (2008).
Michael R. Hamblin, et al., "Photodynamic therapy: a new antimicrobial approach to infections disease?," Photochem. Photobiol. Sci., vol. 3, pp. 436-450 (2004).
V. Sol, et al., "Amino porphyrins as photoinhibitors of Gram-positive and -negative bacteria," Bioorganic & Medicinal Chemistry Letters, vol. 14, pp. 4207-4211 (2004).
Mariana M. Gois, et al., "Susceptibility of *Staphylococcus aureus* to porphyrin-mediated photohynamic antimicrobial chemotherapy: an in vitro study," Lasers in Medical Science, 25(3):391-395 (May 2010).
Clara Comuzzi, et al., "Synthesis and Biological Evaluation of New Pentaphyrin Macrocycles for Photodynamic Therapy," Journal of Medical Chemistry, 49(1):196-204 (Jan. 12, 2006).
Valentina Rapozzi, et al., "Small Interfering RNA-MEdiated Silencing of Glutathione-S-Transferase A1 Sensitizes Hepatic Carcinoma Cells to Photodynamic Therapy with Pentaphyrins." CHEMMEDCHEM, 3(4):565-568 (Apr. 2008).
Maurizio Ballico, et al., "Metallation of pentaphyrin with Lu(III) dramatically increases reactive-oxygen species production and cell phototoxicity," European Journal of Medicinal Chemistry, 46(2):712-720 (Feb. 2011).
Xodo, et al, 2nd European Conference on Chemistry for Life Sciences: Sep. 4-8, 2007 (Cologne).

*Primary Examiner* — Yong Chong
(74) *Attorney, Agent, or Firm* — Abelman, Frayne & Schwab

(57) ABSTRACT

The invention relates to the use of 20-(4-carboxyphenyl)-2, 13-dimethyl-3,12-diethyl-[22] pentaphyrine as antibacterial agent in photodynamic treatment. This expanded porphyrin derivatized in position 4 with a carboxyphenyl group proved very active after photo-oxidation both against *S. aureus* and *E. hirae*. Its high antibacterial activity and its low toxicity make this pentaphyrine particularly useful as antimicrobial agent both for photodynamic therapy against bacterial infections and in the disinfection of microbiologically contaminated liquids.

3 Claims, 6 Drawing Sheets

1

2

● PCCox 5 microM, 24 W/m2 470 nm
▲ PCCox 5 microM, 24 W/m2 470 nm, 1h incubation in the dark

| □ PCCox 0,05 microM, 40 W/m2 | ■ PCCox 0,05 microM, 24 W/m2 470 nm |
| ◇ PCCox 0,5 microM, 40 W/m2 | ◆ PCCox 0,5 microM, 24 W/m2 470 nm |
| △ PCCox 5 microM, 40 W/m2 | ▲ PCCox 5 microM, 24 W/m2 470 nm |

USE OF DERIVATIVES OF PENTAPHYRINE AS ANTIMICROBIAL AND DISINFECTANT AGENTS

RELATED APPLICATIONS

This application is a 371 of PCT/IB2011/053992 filed Sep. 13, 2011 and claims priority from Italian Patent Application No. PD2010A000271 filed on Sep. 13, 2010, both incorporated by reference in their entirety.

FIELD OF THE INVENTION

The invention relates to the use of derivatives of pentaphyrine, and in particular of 20-(4-carboxyphenyl)-2,13-dimethyl-3,12-diethyl-[22] pentaphyrine and metallated derivatives thereof, as antimicrobial agents for photodynamic treatment, both therapeutic of infections, especially bacterial, and sterilizing of liquids, as microbiologically polluted waters, for human and animal use.

PRIOR ART

The increasing resistance of bacteria to antimicrobial agents has promoted research into alternative treatments for treating antibiotic-resistant infections and for preventing the development of resistant strains. One of these is antimicrobial photodynamic therapy (PDT), which constitutes one of the newest and most promising approaches for combating antibiotic-resistant bacteria. At present, it has been demonstrated that both the strains that are sensitive and those that are resistant to antibiotics can be photoinactivated successfully with this therapy. Moreover, it has been demonstrated that repeated photoinactivation of bacterial cells does not lead to selection of resistant strains. This therapy is based on the use of light, of oxygen and of a photosensitive agent (called "photosensitizer" hereinafter). Once the photosensitive agent has been administered the infected tissue is illuminated generally with lamps of 500 or 250 W, inducing activation of the agent administered. In the case when the lesion is internal the light is conveyed into the area of interest by optical fibres. The mechanism of action can be represented schematically as in FIG. 1: the light activates the photosensitive agent, which in its turn promotes the oxygen present to the singlet state. Singlet oxygen is extremely reactive and cytotoxic, being able to interfere with the normal functions of the bacterial cell to the point of causing its death.

Research into new "photosensitizers" aims to develop new photoactive molecules to increase the efficacy of the technique and limit its side-effects. To achieve this objective, it is possible to act either on the photophysical properties of the photosensitizer, or on its affinity for the bacterial wall. The most important characteristics that a photosensitizer must possess are: a) ability to interact with the bacterial membrane; b) strong absorption of light at wavelengths greater than 400 nm (to increase its efficacy in terms of tissue penetration); c) capacity for high yield of singlet oxygen; d) low toxicity in the dark.

A series of molecules was developed in the last decade, designed to promote extremely rapid interaction with bacterial cells and hence a high level of preferential inactivation of pathogens with respect to the main component of the host tissue, for example fibroblasts and keratinocytes in the case of skin infections. These discoveries have opened the way to the use of photodynamic therapy for treating localized microbial infections and for disinfection, principally of microbiologically polluted waters. The majority of photosensitizers that have been or are being investigated for antimicrobial PDT belong to the class of phenothiazines, porphyrins, chlorines and phthalocyanines (M. R. Hamblin, T. Hasan, *Photochem. Photobiol. Sci.*, 2004, 3 436-450; M. Magaraggia, F. Faccenda, A. Gandolfi, G. Jori, *J. Environ. Monit.*, 2006, 8, 923-931. Oliveira, A. Almeida et al. *J. Applied Microb.*, 2009, 106, 1986-1995).

The available information suggests that the presence of positively charged substituents positioned at the periphery of the aromatic backbone of the photosensitizer greatly increases its activity against bacteria. It has been demonstrated, moreover, that antimicrobial activity increases with the number of positive charges present in the meso position (S. Banfi, E. Caruso et al., *J. Photochem. Photobiol. B: Biology* 2006, 85, 28-38; V. Sol, P. Branland, et al. *Biorg. Med. Chem. Lett.* 2004, 14, 4207-4211). The positive charge limits the number and type of photosensitizers that can be designed and therefore the search for compounds that can constitute a novel class of antimicrobial agents for photodynamic therapy is of exceptional interest.

The inventors have for some time been actively engaged in research into expanded porphyrins, i.e. porphyrinoid macrocycles consisting of more than four pyrrole units, and in particular in the synthesis of pentaphyrines and their activity as photosensitizers in the field of oncology. Recently, in fact, they reported the synthesis and antitumour activity of two novel expanded porphyrins belonging to the class of [1.1.1.1.1] pentaphyrines: the non-aromatic macrocycle called isopentaphyrine 1 (with 24 $\pi$ electrons) and the corresponding aromatic macrocycle 2 (with 22 $\pi$ electrons) called pentaphyrine (FIG. 2) (Comuzzi C. et al., *J. Med. Chem.*, 2006, 49, 196-204; Comuzzi C. et al., *Tetrahedron*, 2006, 62 (34): 8147-8151; Rapozzi V. et al., *Chem. Med. Chem.*, 2008, 3, 565-568). The synthesis of isopentaphyrine was obtained by adopting a synthesis strategy based on an acid-catalysed [3+2] condensation. The biological activity of the pentaphyrines was evaluated on four different tumour cell lines (HeLa cervical cancer cells, HepG2 hepatic carcinoma, B78-H1 melanoma, MCF-7 breast cancer). Since the pentaphyrines are fluorescent, it was possible to conduct studies of uptake by confocal laser microscopy and cytofluorometry. These experiments demonstrated that these macrocycles effectively penetrate the cell membranes, becoming localized preferentially in the cytoplasm. In the absence of light, the pentaphyrines are non-toxic up to a concentration of 3 µg/ml. In contrast, pentaphyrines administered to cells at a concentration between 1.5 and 3 µg/ml cause, after irradiation, a considerable dose-dependent phototoxic effect. Experiments conducted on various cell lines demonstrated that both non-aromatic iso-pentaphyrine and aromatic pentaphyrine are potent photosensitizers causing, 24 h after treatment, the death of 60-80% of tumour cells that were treated and irradiated. It was demonstrated in pancreatic tumour cells that apoptosis is the principal mechanism of cellular death triggered by the pentaphyrines. These promising preliminary results constitute the basis for a detailed study of the potential of the class of [1.1.1.1.1] pentaphyrines as photosensitizers in the context of photodynamic therapy. In the course of development of this very promising research, the inventors synthesized a new generation of [1.1.1.1.1] pentaphyrines, by modifying the original structure in order to obtain molecular systems that are more efficient in terms of selectivity for tumour cells, optical properties and phototoxic effect. In particular, a carboxyl group, which might function as a site of attack for specific vectors, was introduced into the structure of the original pentaphyrine (Lesa B. et al., *XXIII International Conference on Photochemistry*. Cologne, 29 July-3

August 2007; Xodo L. et al., *2nd European Conference on Chemistry for Life Sciences*. 4-8 Sep. 2007, Wroclaw (Poland).

SUMMARY

In view of the need for photosensitive agents of low toxicity but with high antibacterial activity that can be repeatedly used without inducing resistance or leading to the development of resistant strains, the inventors have tried whether the novel pentaphyrine substituted in position 20 with a carboxyphenyl group, 20-(4-carboxyphenyl)-2,13-dimethyl-3,12-diethyl-[22] pentaphyrine (abbreviated to PCCox hereinafter), would maintain the properties of pentaphyrine and whether it would be able, after photo-oxidation, to exert antimicrobial activity. In the course of this research, the inventors were able to verify that not only substitution in position 4 does not cause substantial disadvantages from the standpoint of photo-oxidation, but it causes a significant antibacterial activities.

Therefore, in a first aspect the invention relates to pentaphyrine derivatives consisting of 20-(4-carboxyphenyl)-2,13-dimethyl-3,12-diethyl-[22] pentaphyrine and metallated derivatives thereof as antimicrobial agents in photodynamic treatment.

As such, the pentaphyrine compounds can be used in photodynamic therapy of microbial infections, sustained by bacteria, fungi, protozoa, algae, viruses, viroids and prions, both in humans and in animals and in the disinfection of microbiologically contaminated liquids. These uses, therefore, constitute further objects of the invention.

Therefore, the present invention extends to compositions comprising 20-(4-carboxyphenyl)-2,13-dimethyl-3,12-diethyl-[22] pentaphyrine and its metallated derivatives in combination with excipients and/or diluents or other active principles that are acceptable for the uses envisaged for the treatment of infections by systemic or local administration or for the disinfection of biologically contaminated liquids.

The characteristics and advantages of the present invention may be better understood from the detailed description that follows.

DETAILED DESCRIPTION OF THE INVENTION

Figure 1:
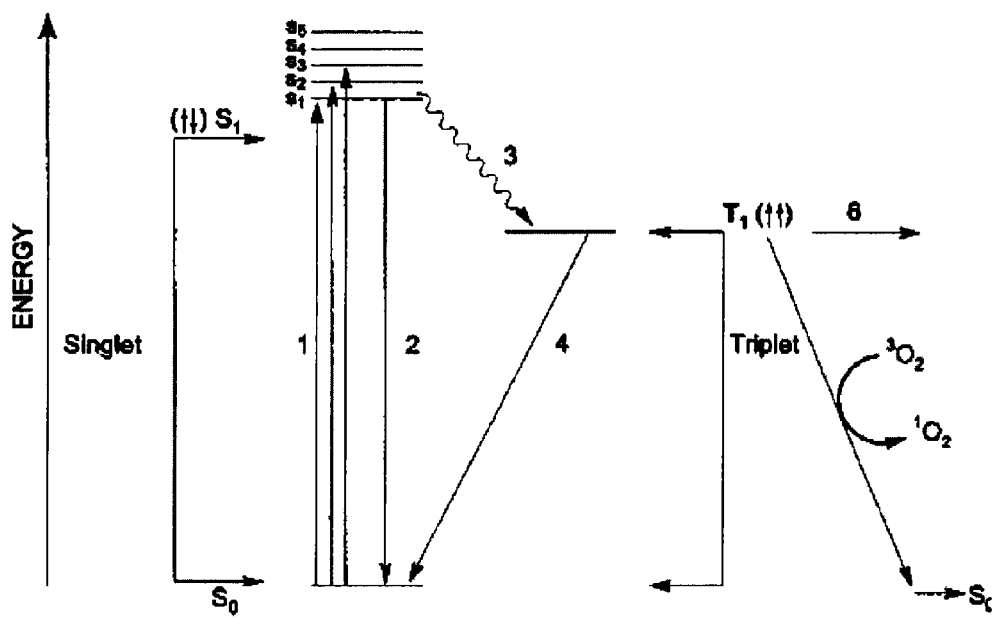
FIG. 1 is a simplified representation of the energy levels and of radiative transitions of a typical sensitizer: 1. absorption of light; 2. fluorescence; 3. intersystem crossing; 4. photophosphorescence; 5. production of $^1O_2$ (type II photo-process); 6. electron transfer (type I photo-process).
Figure 2:
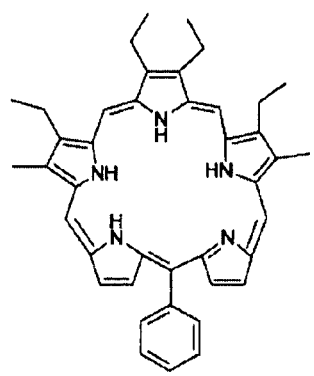
FIG. 2. Non-aromatic macrocycle iso-pentaphyrine 1 (with 24 π electrons) and the corresponding aromatic macrocycle 2 (with 22 π electrons) designated pentaphyrine.
Figure 2:
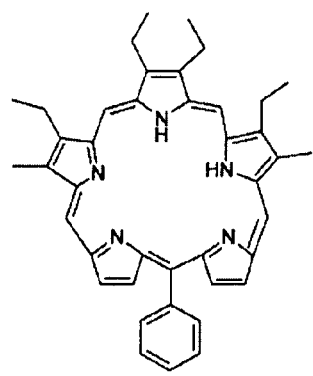

The invention relates to the pentaphyrine substituted in position 20 with a carboxyphenyl group, the structural formula of which is given hereunder

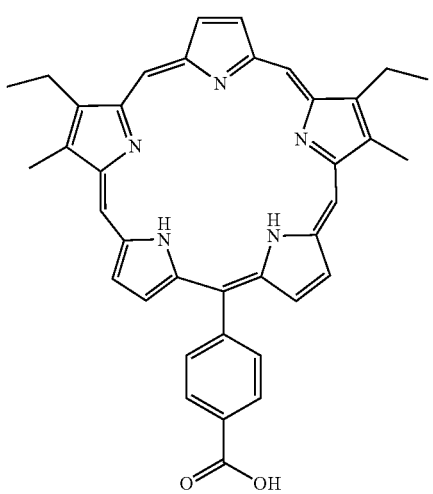 [SMILES: CCC1=C(C)c2cc3ccc([nH]3)c(-c3ccc(C(=O)O)cc3)c3ccc(cc4nc(cc5nc(cc1n2)C=C5)C(CC)=C4C)[nH]3]

20-(4-carboxyphenyl)-2,13-dimethyl-3,12-diethyl-[22] pentaphyrine (PCCox)
and metallated derivatives thereof.

The pentaphyrine compound $PCC_{ox}$ under consideration has been shown to have a significant antimicrobial activity, in particular antibacterial, as a result of photo-oxidation. In fact, it proved extremely active even at nanomolar concentrations reaching 10 log of die-off for solutions containing PCCox 5 µM and illuminated with light sources (blue LED) with maximum emission at 473 nm, and with a fluence rate between 24 and 50 W/m².

Moreover, studies conducted for evaluating antibacterial activity as a result of light activation demonstrated that PCCox does not have bactericidal activity in the dark, thus showing the typical behaviour of a photosensitizer. In fact, bacterial solutions treated with the same light for the same times, but in the absence of PCCox as photosensitizer, give bacterial load die-off equal to 0%. The results obtained, which are presented in detail below, in addition show that already at 30 min of treatment at a concentration of the pentaphyrine PCCox of 0.05 W, 99.9% (3 log) of bacterial load die-off is achieved, while at 5 µM the pentaphyrine PCCox destroys 99.999% of the initial bacterial load ($10^8$-$10^{13}$ CFU/ml) within 15 min of exposure to the light.

Therefore, the pentaphyrine PCCox has been shown to be a compound that can usefully be employed after photo-oxidation as antimicrobial agent, preferably as antibacterial agent, both in photodynamic therapy for treating infections and for disinfection of biologically contaminated liquids, for example water.

Moreover, as it is known that the expanded porphyrins can complex metals by interaction with the nitrogens of the pyrrole rings, the invention also relates to the metallated derivatives of 20-(4-carboxyphenyl)-2,13-dimethyl-3,12-diethyl-[22] pentaphyrine. For the purposes of the present invention the preferred metals can be selected from Si, Ge, Lu, Yb, Ln, Al, Mn, Fe, Ru, Hg, Zn, Cu, Mg, Ni, Pd, Pt, Ag and Au. Among these metals, those preferred are zinc, ruthenium, the lanthanides, silver and gold, also in unusual states of oxidation. The pentaphyrine derivatives having a carboxyl group can also be in the form of salts preferably with alkali metals such as sodium and potassium.

For these uses, the pentaphyrine PCCox and its metallated derivatives can be used for preparing compositions both for human and veterinary use as is known by a person skilled in the art with diluents and/or excipients, suitable and acceptable for the uses envisaged and for the type of administration envisaged, at concentrations varying according to the applications and the required antimicrobial effects. From the results achieved it is quite clear that concentrations between 0.05 µM and 5 µM can be envisaged.

Depending on the type of infection or contamination, the pentaphyrine compounds PCCox and the metallated derivatives thereof can, in addition, be combined in the same compositions with other known, specific antimicrobial active principles depending on the type of microorganism responsible for the infection.

The use of the pentaphyrine PCCox and its metallated derivatives as photosensitizer in photodynamic therapy offers numerous advantages respect to the photosensitizers used until now. This pentaphyrine in fact shares the following characteristics with the other pentaphyrines:

it has strong absorption at wavelengths >470 nm which corresponds to greater tissue penetration relative to the porphyrins;

it has high stability in the solid state;

it has extremely low intrinsic toxicity;

it permits stable conjugation of metals. This increases the efficiency in terms of production of singlet oxygen.

There now follow some examples of carrying out the invention and evaluation of the benefits derived from the invention, which are given as non-limiting illustration of the invention.

EXAMPLES

Example 1

Synthesis and characterization of 20-(4-carboxyphenyl)-2,13-dimethyl-3,12-diethyl-[22] pentaphyrine (PCCox)

The expanded porphyrin 20-(4-carboxyphenyl)-2,13-dimethyl-3,12-diethyl-[22] pentaphyrine was synthesized according to a synthesis scheme based on an acid-catalysed 3+2 condensation as previously reported for the pentaphyrines and according to the scheme presented hereunder

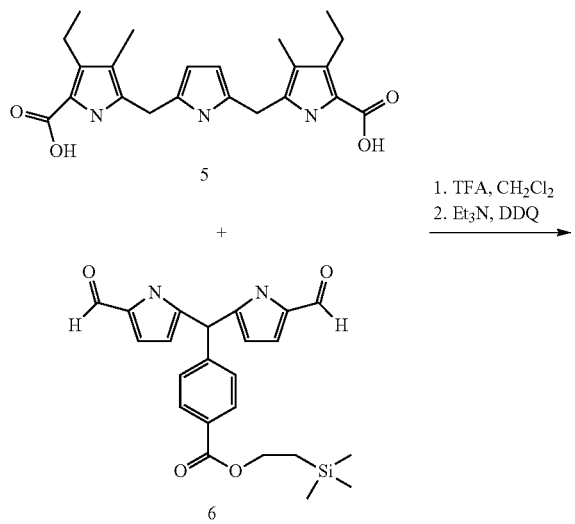

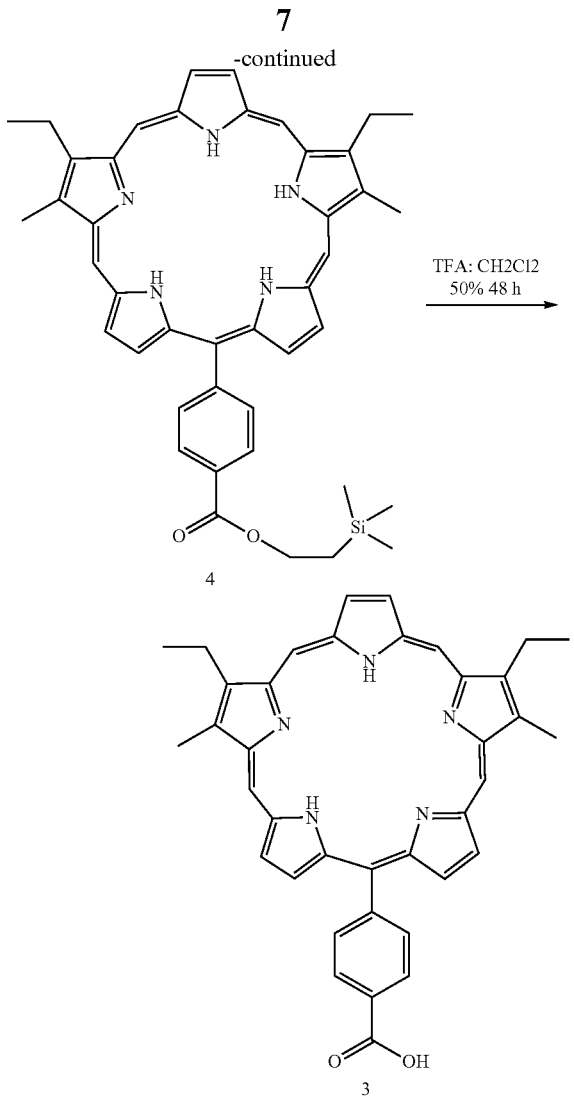

The standard procedure for cyclization envisages that the tripyran 5 is decarboxylated in pure TFA (trifluoroacetic acid) and that to this solution, diluted to 200 times with $CH_2Cl_2$, the dipyran unit 6, bearing the carboxyl function, suitably protected, is added in the dark (Comuzzi et al., 2006, ref. cit.; Lindsey et al., Tetrahedron, 1994, 50, 8941-8968; Rao et al., J. Org. Chem., 2000, 65, 1084-1092; Brines et al. Tetrahedron, 2002, 58, 4375-4381). After the reaction mixture has been neutralized with triethylamine, DDQ (2,3-dichloro-5,6-dicyanobenzoquinone) (2 eq) is added as oxidizing agent. The organic phase is extracted with brine. The raw reaction product is purified on a C18 column by flash chromatography. (Trimethylsilyl)ethoxycarbonyl)phenyl-2,13-di methyl-3, 12-diethyl-[24]isopentaphyrine 4 (PCCRedProt) is obtained at a yield of 50%. PCCRedProt 4 is then fully oxidized to PCCox 3 by exposing a solution thereof in $CH_2Cl_2$, containing 50% of trifluoroacetic acid (TFA), to the air for 48 hours. In this step, in addition to complete oxidation of the molecule, there is also deprotection of the carboxyl function. The need to add acid to obtain total oxidation of the pentaphyrine was confirmed by cyclic voltammetry measurements. The data show that the oxidation of PCCRedProt 4 to PCCox 3 takes place at a potential +2.4V vs Ag/AgCl, NaCl sat/MeCN, 0.05 M $NBu_4ClO_4$. Addition of acid (TFA) causes advance of the potential to +1.4V suggesting possible conversion of PCCRedProt 4 to a more easily oxidizable form.

The pentaphyrine 3 and PCCRedProt 4 were fully characterized.

Pentaphyrine 3

ESI-MSn: $MH^+$: 592; $MH^+.H_2O$: 610; $MH^+.CH_3OH$: 624.

UV-Vis in 100% TFA shows a Soret band at 460 nm (log $\epsilon$=5.13) in the Q-band zone at 647 nm (log $\epsilon$=3.96) and 797 (log $\epsilon$=3.58). In $CH_2Cl_2$ 33% TFA shows a Soret band at 459 nm (log $\epsilon$=5.11) and Q-band at 800 nm (log $\epsilon$=3.61).

$^1$H NMR 200 MHz ($CDCl_3$, 50% TFAH) 12.85 (s, 2H, meso-CH); 12.77 (s, 2H, meso-CH); 11.37 (s, 2H, H pyrrole); 10.75 (d, 2H, H pyrrole); 10.00 (d, 2H, H pyrrole); 8.12 (d, 2H, H phenyl); 7.43 (d, 2H, H phenyl); 4.99 (q, 4H, $CH_2$ ethyl); 4.5 (s, 6H, $CH_3$); 2.35 (t, 6H, $CH_3$ ethyl); −4.73 (br s, 2H, NH); −4.93 (br s, 1H, NH); −5.07 (br s, 2H, NH);

PCCRedProt 4

$^1$H NMR 200 MHz ($CD_3OD$): δ=9.28 (s, 2H, CH pyrrole), 7.88 (d, 2H, H phenyl), 7.21 (d, 2H; H phenyl), 6.88 (d, 2H, H pyrrole), 5.90 (d, 2H, H pyrrole), 6.52 (s, 1H, meso-CH), 5.60 (s, 1H; meso-CH), 4.32 (t, 2H; $CH_2\underline{CH_2}O$), 3.16 (q, 4H, C$\underline{H_2}CH_3$), 1.26 (s, 6H, $CH_3$), 1.04 (t, 2H, $CH_2\underline{CH_2}Si$), 0.81 (t, 6H, $CH_2C\underline{H_3}$), −0.009 (s, 9H; Si($C\underline{H_3}$)$_3$).

The pentaphyrine 3 was tested as antibacterial agent. The experimental conditions are given below.

Example 2

Antibacterial Activity of 20-(4-carboxyphenyl)-2,13-dimethyl-3,12-diethyl-[22] pentaphyrine (PCCox)

Bacterial Cultures and Strains Used

The bacterial strains used in the photo-oxidation tests are S. aureus ATCC 6538 and E. hirae ATCC 10541. The bacterial culture in exponential phase is obtained by inoculation in 10 mL of Nutrient Broth No. 2 and incubation at 37° C. Next the culture is centrifuged for 15 minutes at 3200 rpm and the pellet is resuspended in PBS 0.01 M in order to obtain a bacterial concentration equal to about $10^8$ CFU/mL (Abs600≈0.1). This suspension was used for the photo-oxidation tests in the conditions described hereunder.

For the purpose of testing the efficacy of PCCox in the disinfection of real substrates obtained from depuration plants, tests were conducted for photo-bacterial load die-off present in primary effluent. Effluents of this type made it possible to test the disinfectant activity of the molecule on enterococci, a typology of Gram-positive pathogens characterizing said substrate.

Light Sources

The photo-oxidative treatment was carried out using various light sources:

Lamp A: 100 W incandescent lamp, able to irradiate the bacterial suspension with a fluence rate equal to 40 $W/m^2$. The UV component of the luminous radiation is removed by filtering the light through a layer of water equal to 0.5 cm;

Lamp B: blue LED lamp, with maximum emission at 473 nm, connected to a power supply that controls its fluence rate between 24 and 50 $W/m^2$;

Lamp C: lamp with blue LED, with maximum emission at 473 nm, with a fluence rate equal to 10 $W/m^2$;

Lamp D: lamp with red LED, with maximum emission at 635 nm, with a fluence rate equal to 10 $W/m^2$.

The luminous intensity supplied by the light sources was evaluated by radiometer (DeltaOhm HD 2302.0 equipped with LP 471 RAD sensor).

Photo-Oxidative Treatment

Figure 3:
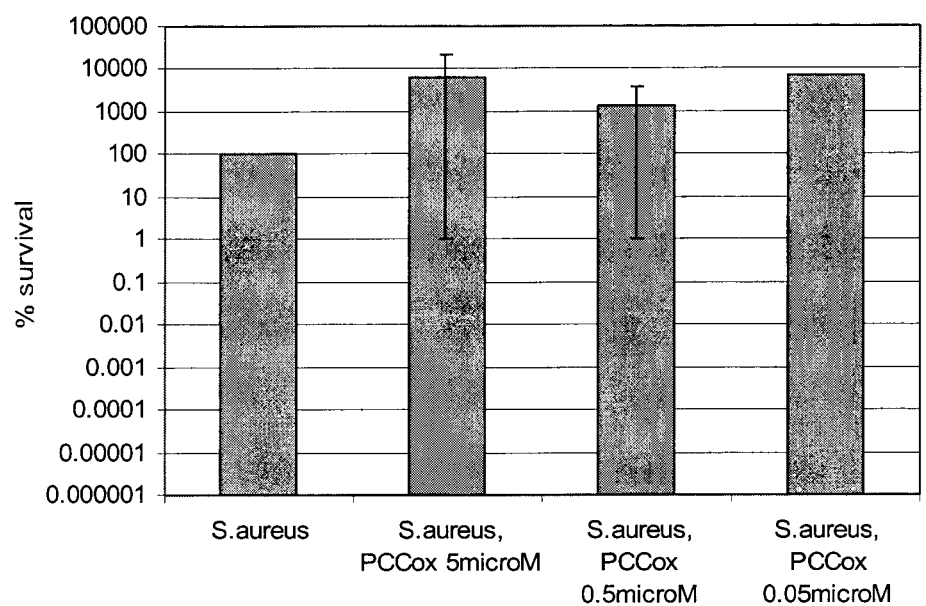
FIG. 3. Toxicity test of the pentaphyrine PCCox evaluating the vitality of a bacterial culture of *S. aureus* incubated for 60 minutes in the dark with various concentrations of 20-(4-carboxyphenyl)-2,13-dimethyl-3,12-diethyl-[22] pentaphyrine (PCCox) (0.05 µM, 0.5 µM and 5 µM).
Figure 4:
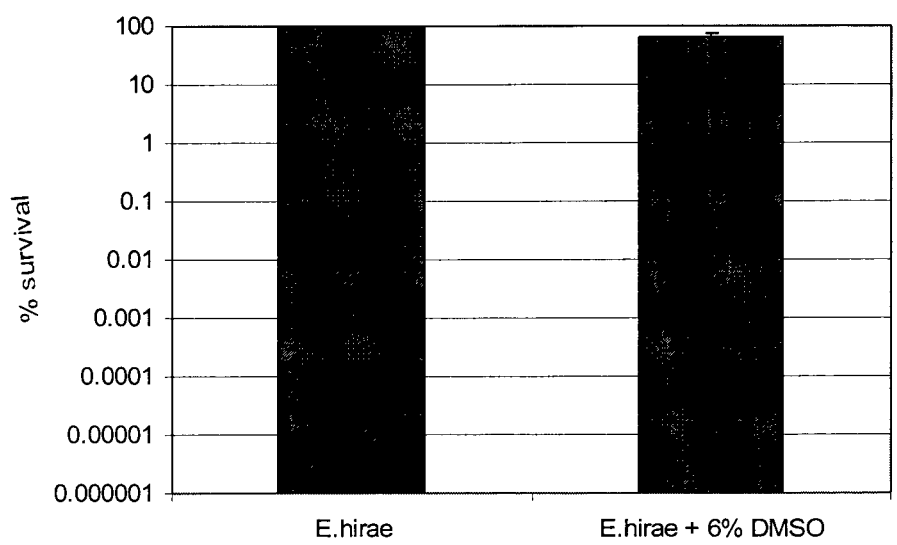
FIG. 4. Toxicity test of DMSO, evaluating the influence of a concentration of DMSO equal to 6% on the vitality of a bacterial culture of *E. hirae*. This is in fact the percentage of DMSO present in solution following addition of the pentaphyrine PCCox at a concentration equal to 20 µM. Both samples were analysed after 120 minutes and the sample incubated with 6% DMSO was submitted to the same conditions of the photo-oxidation tests (with stirring, irradiated with blue light 50 W/m² for 120 minutes).

The photo-oxidation tests were performed on a culture volume equal to 1 mL, using a plate with 48 wells with diameter of 1 cm and capacity of 1.5 mL. The multi-well plate is positioned above a magnetic stirrer and under the light source. A volume of a 330 μM solution of PCCox in DMSO is added to the bacterial suspension in order to obtain various concentrations of the photosensitizer (0.05 μM, 0.5 μM, 5 μM and 20 μM). The solution is stirred by small magnetic anchors throughout the treatment. The intrinsic toxicity, i.e. the toxicity not induced by the light, of the PCCox was evaluated on bacterial cultures of S. aureus and E. hirae incubated for 60 minutes in the dark with various concentrations of PCCox: in FIG. 3 are reported the results obtained on S. aureus; similar results were obtained with E. hirae. The percentage of DMSO present in the culture treated never exceeds 6%. The toxicity tests of DMSO performed on bacterial cultures of S. aureus and E. hirae showed that this percentage of DMSO is not toxic to the bacteria. In FIG. 4 are reported the results obtained with E. hirae; similar results were obtained with S. aureus.

Duration of the Photo-Oxidative Treatment

The duration of the treatment is different for S. aureus (15, 30 and 60 minutes) and E. hirae (60 and 120 minutes).

Figure 5:
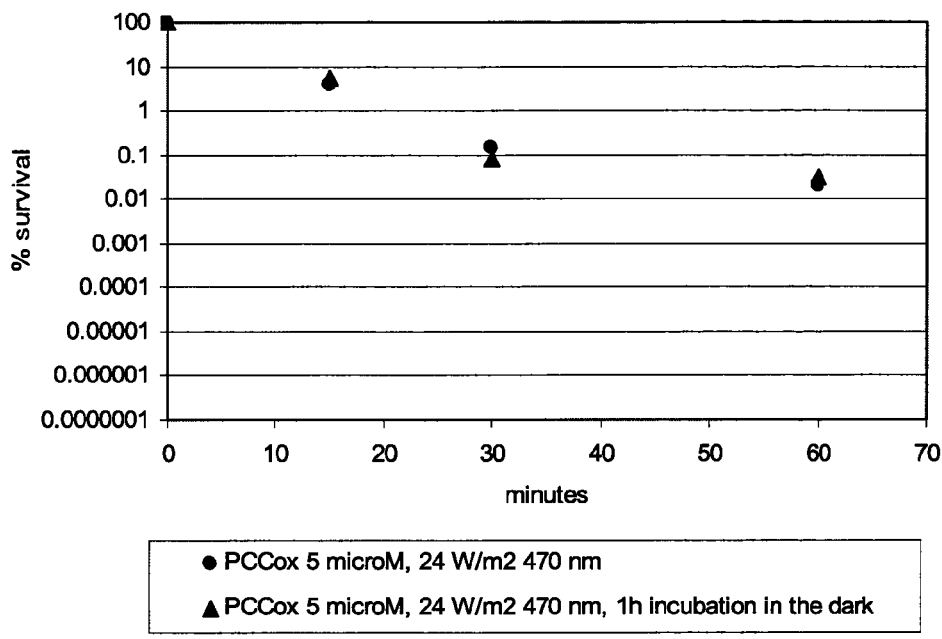
FIG. 5. Photo-oxidation test for evaluating the antibacterial activity of the pentaphyrine PCCox (concentration in solution 5 µM) on *S. aureus* at various incubation times (•) in comparison with the antibacterial activity obtained after pre-incubation of the bacterial culture with the molecule in the dark for 1 h (▲). The test was carried out with a source of blue light (maximum emission at 473 nm) at a luminous intensity equal to 24 W/m².

The influence of a step of incubation of the bacterial culture in the dark in the presence of the molecule was evaluated before the irradiation step. In FIG. 5 are reported the results obtained with S. aureus.

Analysis of the Samples

At each time interval, a volume of bacterial suspension of 100 μL is taken and is diluted in PBS 0.01 M using an optimum dilution factor for the bacterial culture. From each dilution, 100 μL of bacterial suspension is taken (1000 μL is taken from the samples of primary effluent), seeded in MSA medium for S. aureus and Mf-Enterococcus Selective Agar for E. hirae on Petri dishes and incubated in the dark at 37° C. for 18-24 hours. The same procedure is carried out for the control samples, used for testing the activity of PCCox in the dark and the vitality of the bacterial suspension, without photosensitizer, exposed to the light or incubated in the dark. These samples are analysed at the end of the treatment. Each test is carried out at least in triplicate, and the survival data in terms of CFU/mL are expressed as the mean and standard deviation. The percentage survival is calculated respect to the concentration of bacteria measured on the control sample exposed to the light, analysed at the end of the test.

Figure 6:
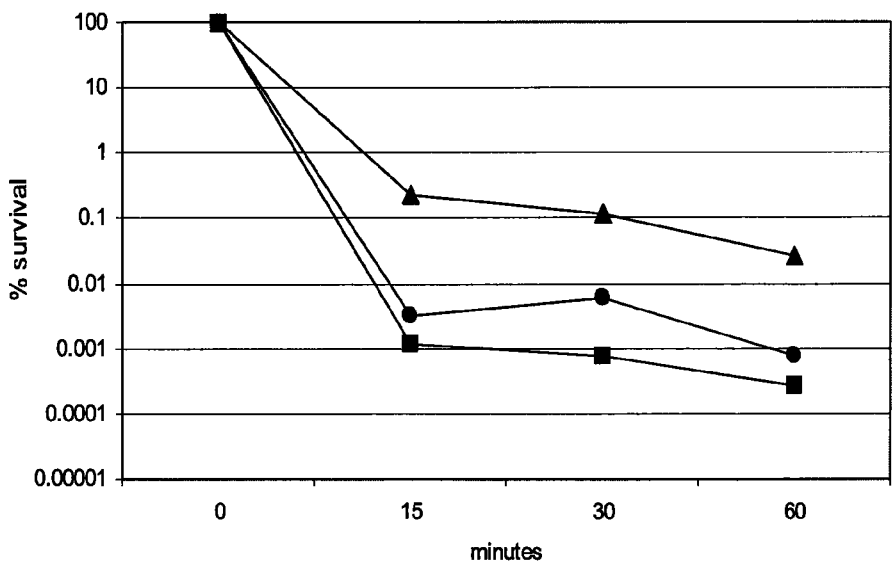
FIG. 6. Mean percentage bacterial survival ($10^8$ CFU/ml initial of *S. aureus*) after illumination with 100 W lamp (fluence rate equal to 40 W/m²) of solutions containing pentaphyrine PCCox, for 15, 30 and 60 min. The experiments were conducted using concentrations of the pentaphyrine PCCox equal to (■) 5, (•) 0.5 and (▲) 0.05 µM.

The results of the experiments conducted with lamp A are summarized in FIG. 6. In terms of percentage die-off, the results, relative to an initial bacterial load equal to $10^8$ CFU/ml, are summarized in Table 1 below.

Table 1. Percentage bacterial load die-off (initial $10^8$ CFU/ml of S. aureus) after illumination of solutions containing PCCox with 100 W lamp (fluence rate equal to 40 W/m$^2$) for 15, 30 and 60 min. The experiments were conducted using concentrations of PCCox equal to 5, 0.5 and 0.05 μM.

| Times (min) | 0.05 μM | 0.5 μM | 5 μM |
|---|---|---|---|
| 15 | 99.77352 | 99.99674 | 99.9988 |
| 30 | 99.88632 | 99.99407 | 99.99921 |
| 60 | 99.97363 | 99.99924 | 99.99973 |

Thus, it can be seen from the results obtained that already at 30 min of treatment at a concentration of the pentaphyrine PCCox of 0.05 μM, 99.9% (3 log) of bacterial load die-off is achieved.

Figure 7:
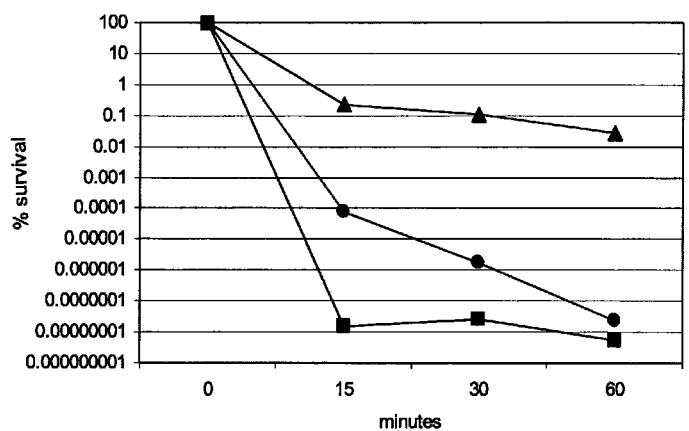
FIG. 7. Mean percentage bacterial survival ($10^{11}$-$10^{13}$ CFU/ml initial of *S. aureus*) after illumination with 100 W lamp (fluence rate equal to 40 W/m²) of solutions containing pentaphyrine PCCox, for 15, 30 and 60 min. The experiments were conducted using concentrations of the pentaphyrine PCCox equal to (■) 5, (•) 0.5 and (▲) 0.05 µM.
Figure 8:
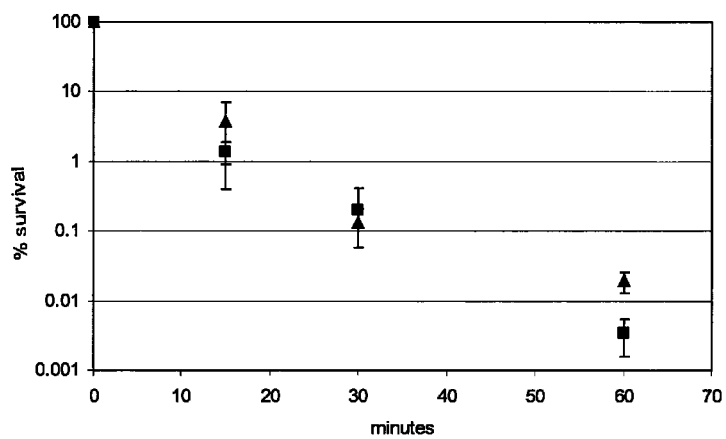
FIG. 8. Survival curves of *S. aureus* after illumination with blue LED lamp at two different fluence rates (▲) 24 W/m² and (■) 50 W/m². All the bacterial cultures contained pentaphyrine PCCox at a concentration equal to 5 µM.
Figure 9:
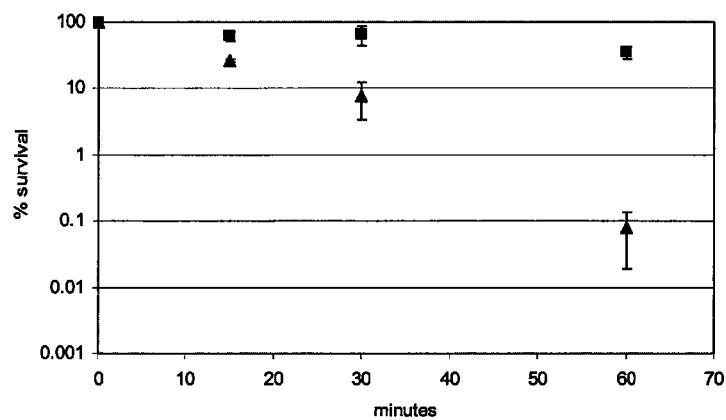
FIG. 9. Photo-oxidation test for evaluating the antibacterial activity of the pentaphyrine PCCox (concentration of solution 5 µM) on *S. aureus* when submitted to illumination with (▲) blue light (maximum emission at 473 nm) and (■) red light (maximum emission at 635 nm) at a luminous intensity equal to 10 W/m². The test was carried out after a prior phase of pre-incubation of the bacterial culture with the molecule in the dark for 1 h.
Figure 10:
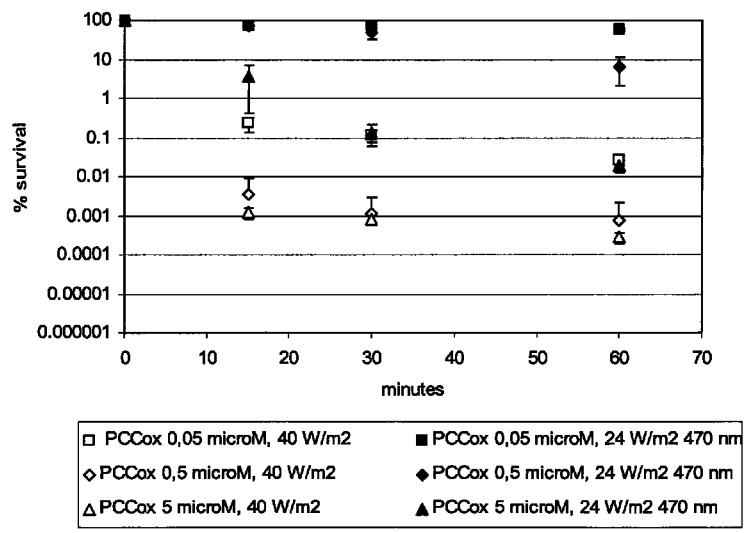
FIG. 10. Photo-oxidation test for evaluating the antibacterial activity of the pentaphyrine PCCox on *S. aureus* as a function of dosage: the bacterial culture was treated with a concentration of PCCox equal to 0.05 µM, 0.5 µM and 5 µM. Moreover, the tests were performed using two different sources of light: white light with luminous intensity equal to 40 W/m² and blue light (473 nm) with luminous intensity equal to 24 W/m².

Similar tests were also performed with initial bacterial load of the order of ($10^{11}$-$10^{13}$ CFU/ml) (FIG. 7). In these experiments the initial bacterial load was increased up to 5 orders of magnitude respect to the experiments in FIG. 6, but maintaining the same concentrations of PCCox in solution. On increasing the bacterial load, the ratio PCCox/bacterial load decreases. Despite this, the bactericidal efficiency of PCCox remains unchanged. As can be seen from the data given in FIG. 7, PCCox remains extremely active even at nanomolar concentrations, reaching 10 log of die-off for solutions containing PCCox 5 μM and illuminated for 60 min with lamp A. This is an extremely interesting result, which suggests that PCCox is not internalized by the bacteria. This result accords with the fact that the bactericidal efficiency is not influenced in any way by the incubation time (FIG. 5). For validating the potential of PCCox as photosensitizer for photodynamic therapy, further experiments were carried out, varying both the fluence rate and the emission spectrum of the lamp. FIG. 8 shows comparison between the data for bacterial load die-off of S. aureus using a lamp B with blue LED (maximum emission at 473 nm) at two different fluence rates: 24 W/m$^2$ and 50 W/m$^2$. The results show that with this type of light, halving the fluence rate does not lead to a drastic decline in bactericidal capacity of PCCox, which is found to be between 4 and 4.5 logs. FIG. 9 shows that on decreasing the fluence rate, i.e. using lamp C with blue LED at 10 W/m$^2$, the bactericidal effect decreases to 3 log (at 60 min of illumination). Finally, FIG. 10 compares the data relating to the bactericidal effect due to PCCox for illumination with lamp A and the data relating to lamp B set at a fluence rate of 24 W/m$^2$. Illumination of the sample with white light leads to an increase in phototoxic efficacy of one logarithmic unit, already reaching 5 log after 15 min of irradiation. If we compare these results with data given in the literature, it can be stated that the [1.1.1.1.1] pentaphyrine PCCox is among the best photosensitizers, being far more active than many neutral photosensitizers and having bactericidal power sometimes comparable and sometimes greater than many cationic systems tested to date.

Figure 11:
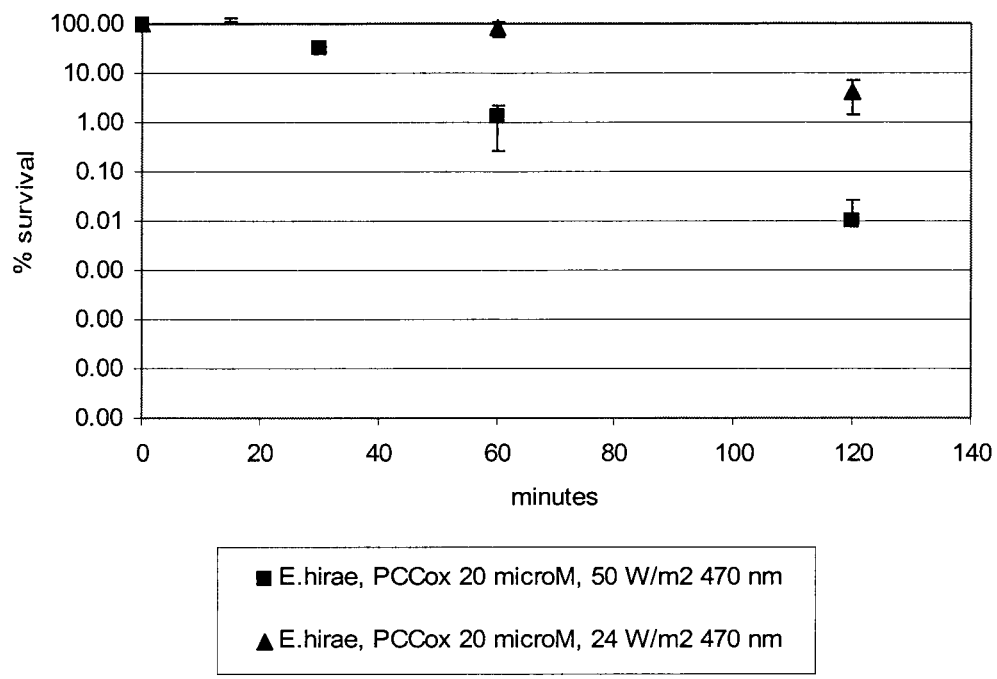
FIG. 11. Photo-oxidation test for evaluating the antibacterial activity of the pentaphyrine PCCox on bacteria *E. hirae*, as a function of dosage and luminous intensity. The bacterial culture was treated with a concentration of PCCox equal to 20 µM. Moreover, the tests were performed using a source of blue light (473 nm) with luminous intensity equal to 50 W/m² and 24 W/m².

For evaluating the efficacy of PCCox on another Gram(+), preliminary tests were conducted on bactericidal activity on E. hirae (FIG. 11). The results show that when PCCox has a concentration equal to 20 μM, 4 log of die-off is attained after 120 min of illumination with lamp B operating at 50 W/m2. This clearly shows that bactericidal efficiency is related to the fluence rate of the lamp.

Figure 12:
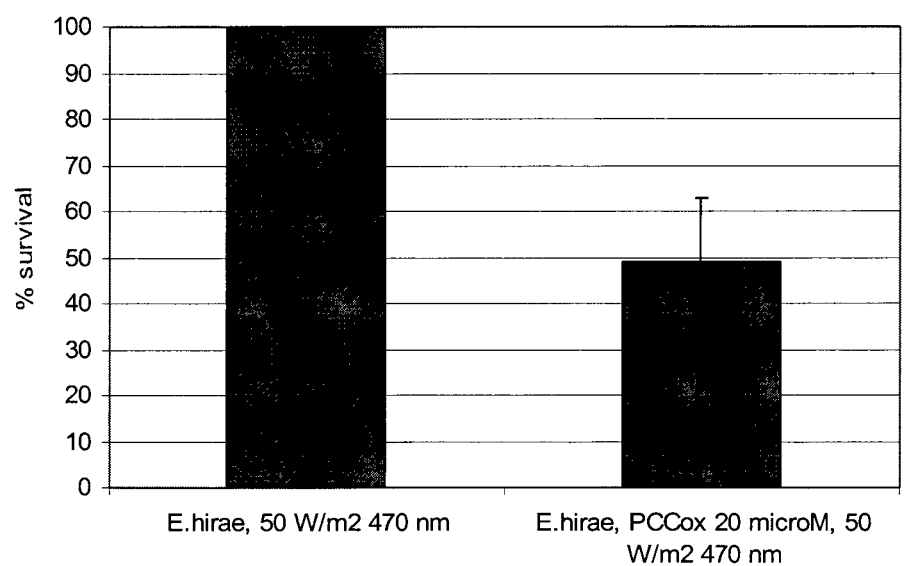
FIG. 12. Photo-oxidation test for evaluating the antibacterial activity of the pentaphyrine PCCox (concentration of solution 20 µM) on a real sample, in this case primary effluent of a purification plant for treating municipal waste. The activity of PCCox was evaluated with respect to the Gram-positive bacterial population of the genus *Enterococcus*, which is present in the sample treated at a concentration equal to $10^4$ CFU/mL. The test was carried out with a source of blue light (473 nm) at a luminous intensity equal to 50 W/m². The percentage survival of enterococci following treatment with PCCox, in the experimental conditions, is equal to 31%.

Finally, FIG. 12 clearly shows that even in complex substrates such as primary wastewater, die-off of up to 70% is achieved in terms of E. hirae.

The invention claimed is:

1. A method of treatment of microbial infections by photodynamic therapy comprising the administration in a subject in a need thereof an effective amount of at least one pentaphyrine selected from the group consisting of 20-(4-carboxyphenyl)-2,13-dimethyl-3,12-diethyl-[22] pentaphyrine, its metallated derivatives and salts thereof.

2. The method of treatment according to claim 1, wherein the microbial infections are bacterial infections.

3. A method of disinfection comprising the treatment with an effective amount of at least one pentaphyrine selected from the group consisting of 20-(4-carboxyphenyl)-2,13-dimethyl-3,12-diethyl-[22] pentaphyrine, its metallated derivatives and salts thereof of, a microbiologically contaminated liquid.

* * * * *